(12) United States Patent
Lazarescu et al.

(10) Patent No.: US 11,048,008 B2
(45) Date of Patent: Jun. 29, 2021

(54) CAPACITIVE SENSOR AND METHOD FOR SENSING CHANGES IN A SPACE

(71) Applicant: SISVEL TECHNOLOGY S.R.L., None (IT)

(72) Inventors: Mihai Teodor Lazarescu, Turin (IT); Akhmareh Alireza Ramezani, Turin (IT); Luciano Lavagno, Turin (IT)

(73) Assignee: Sisvel Technology S.R.L., None (IT)

( * ) Notice: Subject to any disclaimer, the term of this patent is extended or adjusted under 35 U.S.C. 154(b) by 203 days.

(21) Appl. No.: 16/098,375

(22) PCT Filed: May 3, 2017

(86) PCT No.: PCT/IB2017/052568
§ 371 (c)(1),
(2) Date: Nov. 1, 2018

(87) PCT Pub. No.: WO2017/191573
PCT Pub. Date: Nov. 9, 2017

(65) Prior Publication Data
US 2019/0170891 A1 Jun. 6, 2019

(30) Foreign Application Priority Data
May 3, 2016 (IT) .................... 102016000045301

(51) Int. Cl.
*G01V 3/08* (2006.01)
*G08B 13/26* (2006.01)
(Continued)

(52) U.S. Cl.
CPC ............. *G01V 3/08* (2013.01); *G01V 3/088* (2013.01); *G08B 13/26* (2013.01); *G08B 21/22* (2013.01); *A61B 5/1113* (2013.01)

(58) Field of Classification Search
CPC ......... G08B 13/26; G08B 21/22; G01V 3/088
See application file for complete search history.

(56) References Cited

U.S. PATENT DOCUMENTS

2003/0083795 A1* 5/2003 Stanley ............. B60R 21/01516
701/45
2011/0310051 A1* 12/2011 Souchkov ............. G06F 3/0418
345/174
(Continued)

FOREIGN PATENT DOCUMENTS

BE 493370 A 5/1950
WO 2006/071578 A2 7/2006
(Continued)

OTHER PUBLICATIONS

International Search Report and Written Opinion dated Sep. 12, 2017, issued in PCT Application No. PCT/IB2017/052568, fled May 3, 2017.

*Primary Examiner* — Alvaro E Fortich
(74) *Attorney, Agent, or Firm* — Workman Nydegger (57) ABSTRACT

A system for localizing an object of interest in a monitored space includes a plurality of capacitive sensors for sensing changes in the status of a space, adapted to electrically interact in a contactless way with a ground surface so as to provide a capacitance varying on the basis of such changes, and adapted to detect at least a time evolution of the capacitance and to produce a capacitance-depending signal, a filtering unit configured for reducing the noise level in the time evolution of such capacitance by filtering the capacitance-depending signal provided by the capacitive sensors, so that corresponding filtered signals are produced, and a central device in signal communication with the capacitive sensors. The central device is configured for acquiring the filtered signals of each capacitive sensor, and for determining the position of the object of interest inside the space by inferring at least a distance of the object on the basis of the filtered signals acquired from at least one of the sensors detecting the object, and by combining the at least a distance
(Continued)

with positional data defining the positions of the plurality of capacitive sensors in the monitored space.

16 Claims, 8 Drawing Sheets

(51) Int. Cl.
*G08B 21/22* (2006.01)
*A61B 5/11* (2006.01)

(56) References Cited

U.S. PATENT DOCUMENTS

| | | | |
|---|---|---|---|
| 2012/0268416 A1* | 10/2012 | Pirogov | G06F 3/0446 345/174 |
| 2013/0038339 A1* | 2/2013 | Peterson | G06F 3/044 324/679 |
| 2014/0002409 A1* | 1/2014 | Rohozin | G06F 3/0488 345/174 |
| 2014/0267157 A1 | 9/2014 | Dorfner | |
| 2015/0002443 A1* | 1/2015 | Brunet | G06F 3/0445 345/174 |
| 2015/0242009 A1* | 8/2015 | Xiao | G06F 3/0416 345/174 |
| 2015/0327687 A1 | 11/2015 | Chacon | |
| 2015/0346862 A1* | 12/2015 | Schwartz | G06F 3/0418 345/174 |

FOREIGN PATENT DOCUMENTS

| | | |
|---|---|---|
| WO | 2006/138008 A2 | 12/2006 |
| WO | 2013/058332 A1 | 4/2013 |

\* cited by examiner

Prior Art

CAPACITIVE SENSOR AND METHOD FOR SENSING CHANGES IN A SPACE

BACKGROUND OF THE INVENTION

Field of the Invention

In its most general aspect, the present invention relates to a system and a method for localizing at least one object of interest in a monitored space, in particular for sensing, preferably in an indoor environment, the presence and the (approximate) position of persons, electrically conductive elements, sources of electric noise, or the like.

Description of Prior Art

It is well-known that the capacitive sensors allow implementing tag-less sensing techniques for indoor monitoring. To be effective and easily adopted, the sensing technique needs to be privacy-aware, tag-less, small-size, low-cost, low-power, reliable, easy to install. Besides long-range capacitive sensing, several other techniques can be used: passive infrared, pressure, ultrasonic Doppler-shift, ultrasonic echo, RF ultra-wide band, infrared camera, etc. Each of them has specific advantages and disadvantages for indoor activity monitoring for the application domains of interest. For instance, the Canary system (https://www.canarycare.co.uk/) uses passive infrared (PIR) based sensors to monitor the activity of a person. This is error-prone because, for instance, PIR-based sensors detect only movements (thus not still activities like watching TV), they operate only within unobstructed line of sight, they do not measure the distance and are prone to false positives due to other heat sources (e.g., pets, sun, stove, or the like).

Capacitive sensors use capacitive transducers that can operate in one of the following modes:
- load mode—it needs only one plate on the transducer because it uses the human body or any other object of interest as a constant-potential second plate. The distance between the transducer and the body is one of the factors that change its capacitance;
- transmit mode—it uses transducers with two plates. In order to detect a change of position, the human body needs to be closely coupled with one of the plates thus varying the apparent distance between the plates during the change of position;
- shunt mode—it uses transducers with two plates. The human body partially shields the electrical field between the plates.

The last two modes (transmit and shunt) are not suitable for the application domains considered in this specification, because they require at least two galvanically coupled plates, which would significantly increase the complexity and the cost of the installation; hence, the first operation mode (load mode) is best suited from this point of view. However, according to the state of the art, the load mode capacitive sensors are limited to ranges comparable with the dimensions of the transducer, which are too short for the typical transducer sizes acceptable for the application fields of interest.

Capacitive sensing systems for tracking human beings in indoor environments have been proposed in the scientific articles "Device-less capacitive indoors localization and activity tracking system", 8th IEEE International NEWCAS Conference, June 2010 and "TileTrack: Capacitive human tracking using floor tiles", IEEE International Conference on Pervasive Computing and Communications, March 2009. Both these systems have the disadvantage to need burdensome installation of capacitive sensing devices in the floor of the building, which increases the costs and the installation time, as well as the inconveniencies caused to the building property. In addition, the number and extent (size) of the capacitive sensing devices is high since it depends on the surface to be covered.

The existing small-size capacitive sensors operating in load mode have a reduced sensing range, typically from near contact up to about 10 cm. Electric and electromagnetic noise and nearby conductive objects interfere with the operation of the capacitive sensors and limit their accuracy and/or sensing range.

Figure 1:
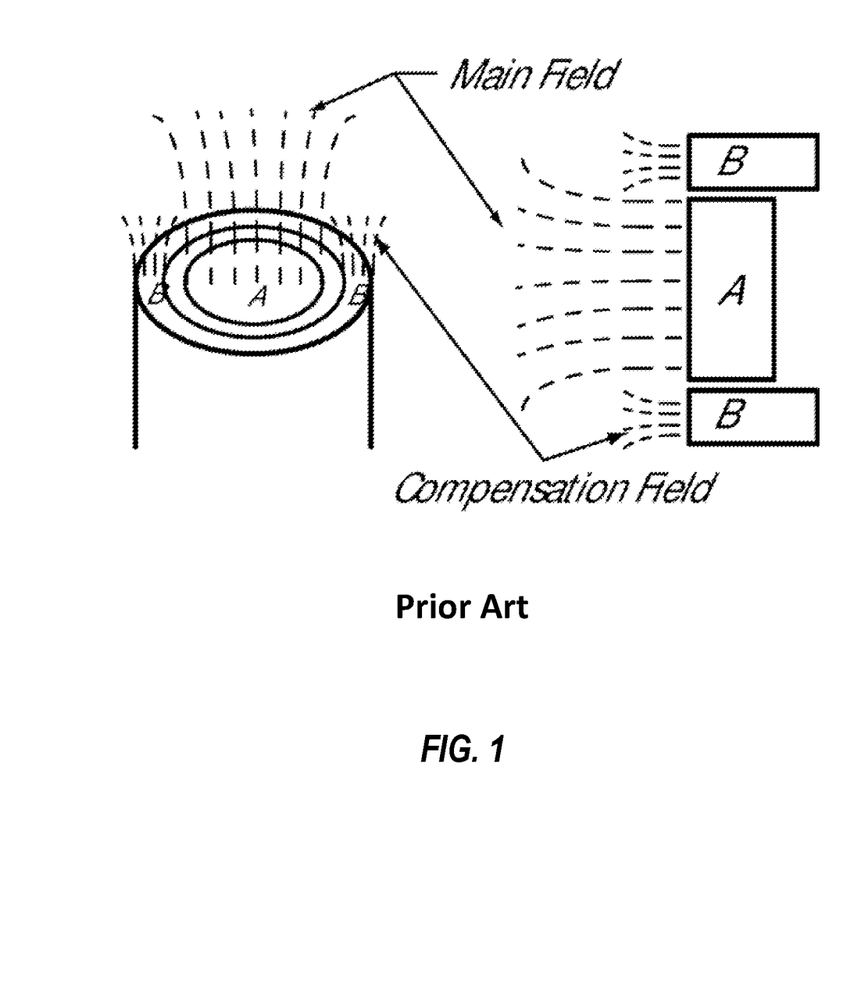
FIG. 1 shows a solution according to prior art for shielding high sensitivity load mode capacitive sensors from the influence of nearby conductive bodies.

To be used for indoor activity monitoring, the sensing range should be in excess of 1 m. However, the existing method used to shield high sensitivity load mode capacitive sensors from the influence of nearby conductive bodies cannot be extended for longer ranges using small-size transducers. The method shown in FIG. 1 makes use of compensation fields that surround the main (measurement) field and are driven by the measurement circuit exactly the same way as the sensing field. These fields maintain noise- and interference-free electrical conditions at the interface with the inner main (measurement) field while allowing the external environment to interfere only with their outer layers. Because the integrity of the compensation fields degrades rapidly with the distance, this technique is effective just up to a few centimeters for small-size transducers.

SUMMARY OF THE INVENTION

The present invention aims to solve these and other problems by providing a system for localizing at least one object of interest in a monitored space.

Furthermore, the present invention aims to solve these and other problems by providing a method for localizing at least one object of interest in a monitored space.

A significant aspect of the present invention is the filtering of a time evolution of the capacitance detected by a load mode capacitive sensor, in order to reduce the noise level of said time evolution of the detected capacitance.

This significantly extends the range of capacitive sensors according to the invention without increasing their size, in particular without extending the surface of the sensing plate of a capacitive sensor.

The capacitive sensor that we propose for tag-less long-range sensing for our target application fields is made of a small-size capacitive transducer operating in load mode and a novel combination of several data processing techniques used to significantly increase the sensing range of the capacitive sensor, well beyond that of existing load-mode small-size capacitive sensors. The ranges of these new capacitive sensors are thus suitable for low-cost applications that require tag-less low-power indoor monitoring of the presence and approximate location of humans, electrically conductive elements or sources of electric noise, for which the existing small-size load-mode capacitive sensors cannot be used.

Further advantageous features of the present invention are the subject of the attached claims.

BRIEF DESCRIPTION OF DRAWING

The features of the invention are specifically set forth in the claims annexed to this description; such characteristics will be clearer from the following description of a preferred and non-exclusive embodiment shown in annexed drawings, wherein:

DETAILED DESCRIPTION OF THE INVENTION

In this description, any reference to "an embodiment" will indicate that a particular configuration, structure or feature described in regard to the implementation of the invention is comprised in at least one embodiment. Therefore, the phrase "in an embodiment" and other similar phrases, which may be present in different parts of this description, will not necessarily be all related to the same embodiment. Furthermore, any particular configuration, structure or feature may be combined in one or more embodiments in any way deemed appropriate. The references below are therefore used only for simplicity's sake, and do not limit the protection scope or extension of the various embodiments.

Figure 2:
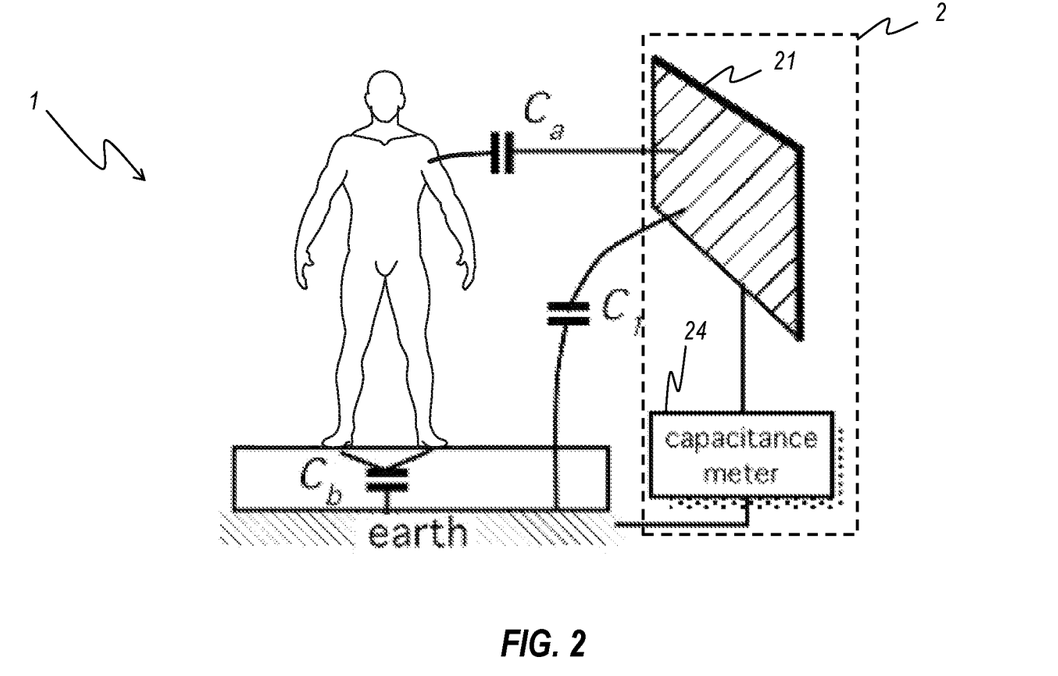
FIG. 2 shows a capacitive sensor according to an embodiment of the invention and an electric model depicting the capacitances sensed by said sensor.

With reference to FIG. 2, a capacitive sensor 2 according to an embodiment of the invention comprises a sensing plate 21 (also referred as "transducer") operating in load mode that creates a capacitance (i.e., electrically interacting with a ground surface so as to show a capacitance) that varies with the distance from a nearby human body and from other static and moving objects, which must be discriminated from the human body of interest via several signal processing techniques.

The capacitance of the transducer is measured using a detecting unit 24, which is comprised in said sensor 2, such as a capacitance meter preferably comprising a relaxation oscillator whose frequency depends on the capacitance of the transducer. Such transducer produces a capacitance-depending signal.

However, the sensitivity of the capacitive transducer steeply decreases with the distance. For long ranges, it decreases approximately proportional to the square or cube of the inverse of the distance. For instance, laboratory measurements show that the variation of the capacitance of a transducer using a 4 cm×4 cm metallic plate due to the presence of a human body at 10 cm in front of it is about 1% (10E-2) of the total capacitance, while at 1 m it drops to about 100 ppm (10E-4), which is hardly distinguishable from the environmental noise (and is consistent with a quadratic decrease with the distance) and from the capacitances C1 (capacitance between metallic plate 21 and earth) and Cb (capacitance between a human body and earth), which are both sensed by said capacitive transducer. Ca is the capacitance between the plate and the body.

Thus, to discriminate small variations of the capacitance of the transducer from the noise, the measurements are processed using a chain preferably comprising the following functional blocks (further details are provided in the following of this specification):

- a capacitive transducer that operates in load mode;
- a capacitance—frequency converter, preferably comprising an astable multivibrator oscillating with a variable period whose oscillation period directly depends on the capacitance $C_a$ of the transducer; the electrical signal produced by the multivibrator is a capacitance-depending signal;
- a direct digital conversion of the frequency, by counting the number of multivibrator periods during the chosen sampling period; so also the signal produced by the conversion is still capacitance-depending;
- decimation and average units to reduce both the quantization noise introduced by the digital conversion and the environmental noise captured by the transducer, and also to increase measurement resolution;
- a set of filters to detect slow changes in position (steady state);
- a set of filters to detect fast changes in position (movements);
- a post-processor of the filter output data to calculate the distance between the sensor and the element of interest (e.g., a human body, a large conductive object, or the like) and its variation over time.

Figure 3:
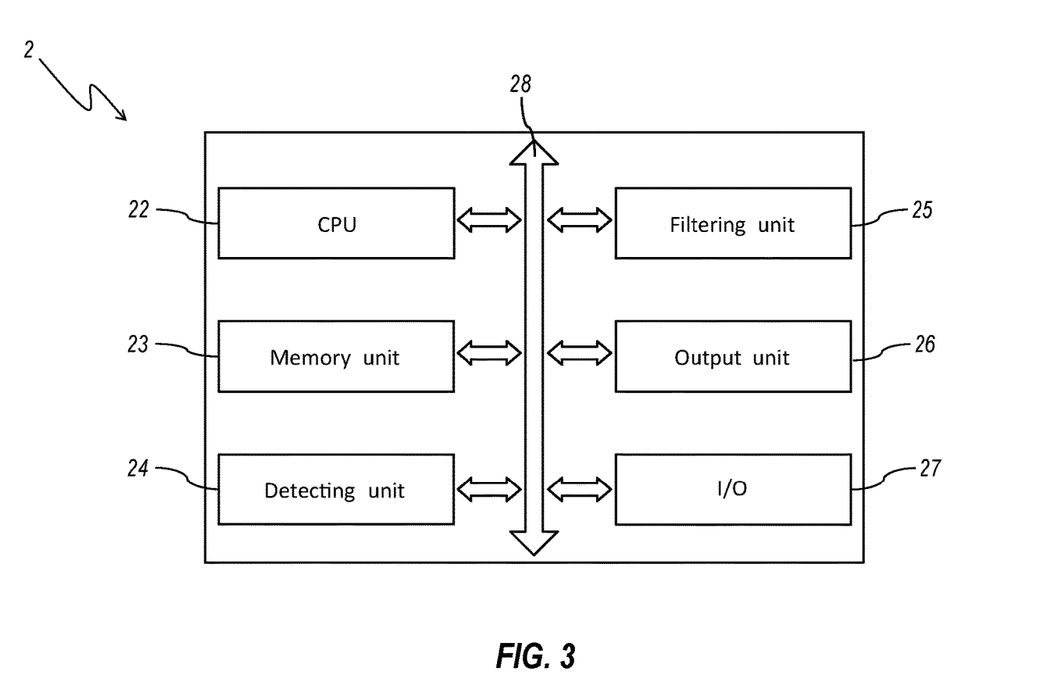
FIG. 3 shows a block diagram of the internal architecture of the capacitive sensor depicted in FIG. 2.

With also reference to FIG. 3, an embodiment of the capacitive sensor 2 also comprises the following parts:

- processing unit 22, like a Central Processing Unit (CPU), configured for executing a set of instruction for carrying out a method for sensing changes in a space through said capacitive sensor (said method will be described in details in the following of this description);
- memory unit 23 containing at least filtering information allowing to reduce noise level in the data gathered by the sensing plate 21, and preferably the instructions that implement the method for sensing changes in a space through said capacitive sensor;
- the detecting unit 24, which has been already described above;
- filtering unit 25, like a Digital Signal Processor, a set of inductive, resistive and/or capacitive components, or the like, configured for reducing the noise level of the signal gathered via the detecting unit 24, in order to increase the sensing distance of said capacitive sensor;
- output unit 26, which is adapted to output a filtered signal produced by the filtering unit 25, preferably indicating the occurring of a change in the space surrounding the sensor 2;
- for this purpose, the output unit 26 may comprise, for example, Bluetooth, NFC (Near Field Communication), Wi-Fi or other adapters, like an adapter capable to receive according a CDMA (Code Division Multiple Access) modulation, or the like;
- I/O unit 27, which can be used, for example, for updating the set of instructions for carrying out the method for sensing capacitive changes in the status of a space according to the invention and/or checking the status of said sensor 2 and/or servicing said sensor 2; for this purpose, the I/O unit 16 may comprise, for example, a USB (Universal Serial Bus) port, a Firewire port, an RS232 or IEEE 1284 port, an Ethernet port, Wi-Fi or other wireless adapters;

a communication bus 28, which allows the exchange of information between the CPU 22, the memory unit 23, the detecting unit 24, the filtering unit 25, the output unit 26, and the I/O unit 27.

As an alternative to using the communication bus 28, the CPU 22, the memory unit 23, the detecting unit 24, the filtering unit 25, the output unit 26, and the I/O unit 27 can be connected by means of a hub architecture. Optionally, these parts 22-28 can be embedded in a microcontroller, an FPGA (Field-Programmable Gate Array), a CPLD (Complex Programmable Logic Device), or the like.

Figure 4:
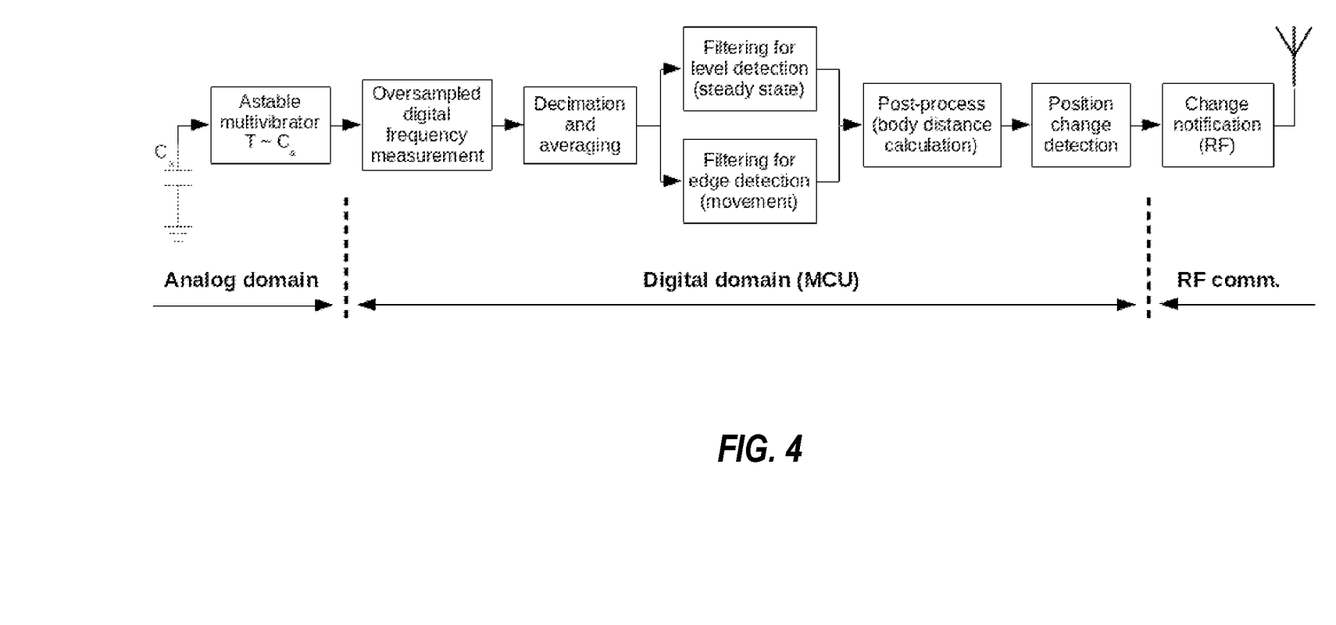
FIG. 4 shows a flow diagram conceptually representing the processing steps performed by a preferred embodiment of the invention.

With also reference to FIG. 4, the capacitive transducer 21 operates in load mode using the element of interest (e.g., the human body, the large conductive object, or the like) as the second plate. Transducer total capacitance thus depends on the distance from the element of interest (e.g., the human body). However, this dependency can be around 0.01% of the total measured capacitance value for the distances necessary for the application domains of interest, and hence much below noise level. Thus, the signal from transducer needs to be processed to extract the distance information with enough accuracy for the application domains.

The period of the oscillator (which in this example uses an astable vibrator, but which could also be implemented using directly the analogue or digital I/Os of a microcontroller or of another digital or analogue circuit) depends (in this case, linearly) on the total capacitance of the transducer.

The period of the oscillator is measured, for example, using a timer on a microcontroller. The measurement also preferably converts the analogue signal into a suitable digital representation, adding quantization noise in the process. The measurement (sampling) rate of the period of the frequency of the oscillator far exceeds the maximum change rate of its variations caused by the condition changes of the monitored space (i.e., it is oversampled). The sampling operation is performed by a frequency measurement unit being part of an Oversample measurement block that converts the oscillation frequency to digital values, allowing to subsequently use digital filters and to obtain the advantages allowed by the digital signal processing techniques. In an embodiment of the invention, the frequency sampling operations are performed by the CPU 22, a microprocessor configured to adapt the frequency values produced by the astable multivibrator to the subsequent signal processing steps.

The Oversample and average block is followed by a digital low-pass filter and a decimation block. In particular, the low-pass filter provides a smoother form of the capacitance-dependent signal, removing the short-term fluctuations, and leaving the longer-term trend; in other words, it extracts the continuous moving component of the measured capacitance, i.e., its average value in time. The decimation is a post-processing step that uses the oversampled signal to increase the resolution of the hardware counter that is used in this case to measure the period of the oscillator (which is strictly related to the frequency) and to reduce the quantization noise introduced by the counting operation.

Each set of filters that follows reduces some specific type of noise. The filter for Level detection is a low pass filter that reduces the high-frequency environmental noise, e.g., coming from electric motors, light switches or the thermal noise from the analogue circuitry. The filter for Edge detection is a high pass filter that reduces the low frequency noise, such as slow variations of the static charge of nearby objects or slow variations of dielectric permittivity due to the level of air humidity. Additional filtering may be used to further increase the immunity to specific types of noise or to increase the sensitivity to specific patterns of the input signal. The cut-off frequency of the low-pass filter is higher than the cut-off frequency of the high-pass filter so as to assure that the useful considered signal is correctly measured in the frequency range in which the capacitance variations are to be measured, because they are considered useful signal and not noise due to events considered insignificant for the application of the capacitive sensing system, i.e., the changes to be detected in the monitored space.

The above processing of the digital signal is necessary to both reduce the various types of noise that affect the measurement, as well as to increase the sensor sensitivity to very small variations of capacitance at the far end of the sensing range. The signal processing chain allows one to significantly extend the measurement range of the capacitive sensor.

Different filter types can be used to better extract different kinds of information from the environment, such as the current position of the person to be tracked, the movement within the room, or the operation of a nearby appliance (e.g., a fridge).

In addition to using different filters, the digital filter blocks can be reconfigured by means of control signals received through the I/O unit 27, in order to extract these different features from sensor environment at different times, for example the person's location when the person is at home, and the correct operation of the fridge when the person is absent for a long period of time. Filter reconfiguration can be done by sending over the air a different set of filter parameters comprised in at least a control signal determining the frequency transfer function to the sensor, such as filter coefficients and number of taps, or by changing the program of the sensor, in part or in full, using over-the-air remote programming techniques such way that the new program implements digital filters with the new filtering characteristics. In other words, the transfer function of the filtering unit can be varied by means of a switching command, and the central device is configured for generating the switching command; the switching command is preferably issued on a wireless communication link.

All the blocks included in the chain (such as the capacitance-driven oscillator) may be preferably implemented on a low-end microcontroller to reduce power consumption, size and cost of the capacitive sensor.

Summarizing, the method for localizing at least an object of interest in a monitored space according to the invention comprises the following phases:

a detection phase, wherein at least a capacitance-depending signal is detected by means of a detecting unit 24, which is in communication with a plurality of sensors 2, wherein said at least one capacitance-depending signal is produced by the time evolution of at least a capacitance that varies on the basis of changes in said monitored space;

a filtering phase, wherein filtered signals are produced by filtering said at least one capacitance-depending signal by means of the filtering unit 25, so that the noise level in said at least one capacitance-depending signals is reduced;

an acquisition phase, wherein said filtered signals are acquired by the central device;

a position determination phase, wherein a position of said object of interest inside said space is determined, by means of said central device, by inferring at least a distance of said object on the basis of the filtered signals acquired from at least one of the sensors 2 detecting said object, and by combining said at least a distance with positional data defining the positions of said plurality of capacitive sensors 2 in the monitored space.

With also reference to FIG. 5, it will now be described an exemplary implementation and the use of a set of sensors 2 to determine the position of a person in a room. The same procedure can be used to determine the position and/or state of another electrically conductive or active element and it will be shown how this can be adapted for uses in other application domains of interest.

Figure 5:
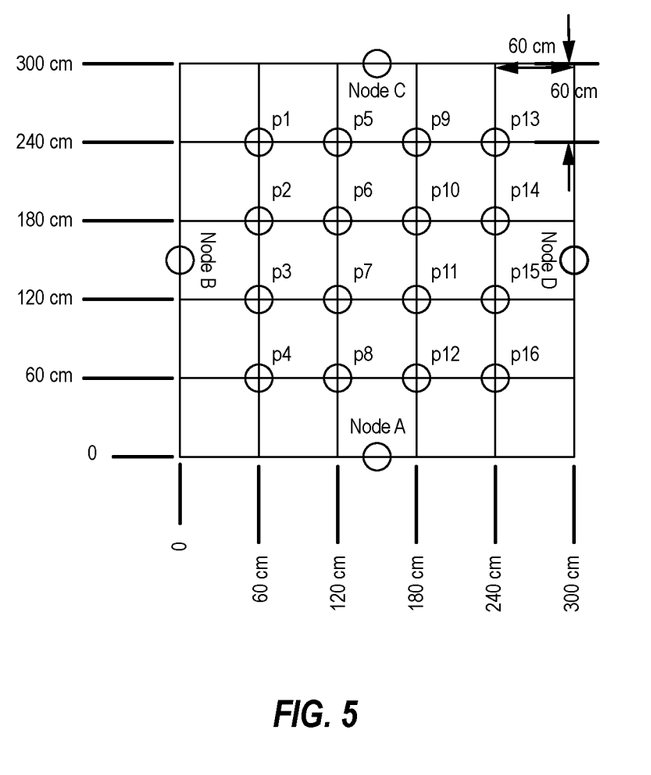
FIG. 5 shows a schematic top view of a room in which four sensors (similar to the one depicted in FIG. 2) are installed.

In this setting, the room is defined as a 3 m×3 m space, and comprises four walls and four sensors 2: each sensor 2 is placed in the middle of one particular wall of the room respectively (shown in FIG. 5 with a circle labeled Node A, Node B, Node C, and Node D). Each sensor has a capacitive sensing element, preferably a sensing plate 21 having an 8 cm×8 cm surface. Transducers plate having size of 4 cm×4 cm and 16 cm×16 cm may also be used. In other words, the sensing plate 21 of the sensor may preferably have a surface extension between 16 and 256 square centimeters. Furthermore, said sensing plate 21 may be preferably square-shaped. The positions of the sensors in such setting are predetermined and known to the central device.

The detecting unit 24 may comprise the following parts:
the capacitive transducer already described above;
a conversion circuit configured for converting capacitance variations detected by the capacitive transducer into frequency variations of an electrical signal. Said conversion circuit is preferably based on the 555 astable oscillator.

The CPU 22 is a microprocessor in signal communication with the detecting and output units, configured for sampling and quantizing the oscillation frequency of the oscillator, for example by using a timer unit configured as a counter, and sending the digital (frequency) reading to a base station (not shown in the attached Figures) by means of the output unit 26, preferably using a wireless transmitter.

The memory unit 23 can store the micro program, i.e., the program code comprising the operating instructions executed by the microprocessor for governing the functioning of the sensor 2, preferably in a non volatile manner. In addition, the unit 23 can store the operating conditions of the various units comprised in the sensor 2, like, for example, commands and operative parameters received from the I/O unit, if present, or to be sent thereto. It can as well store past capacitive values detected by the detecting unit to be transmitted to the base station, and so on.

When a person moves within the room, the capacitances of the transducers of the sensors change due to the variation of the distances between the transducers and the body of the person.

Figure 6:
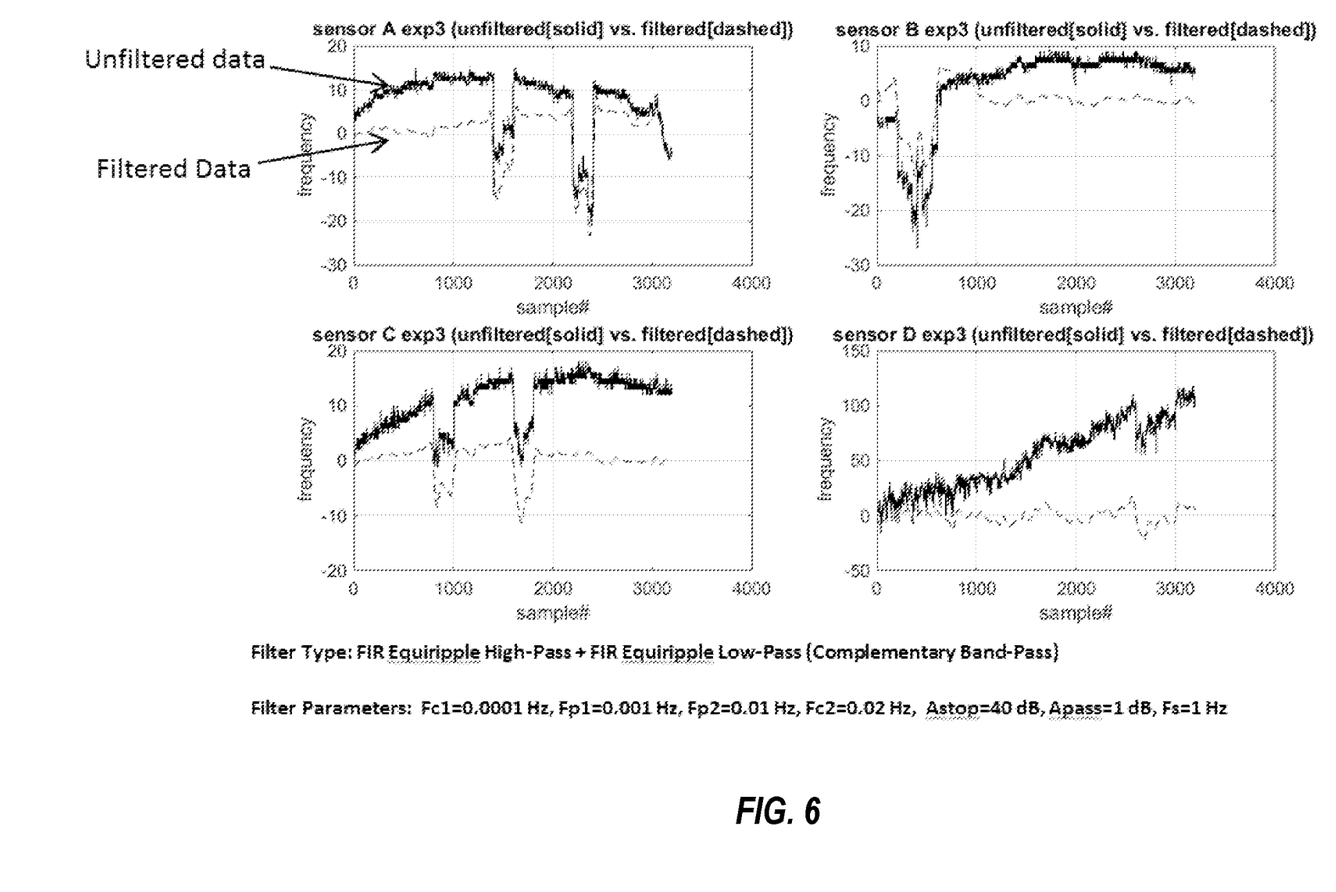
FIG. 6 shows graphs plotting the raw data and the filtered data collected by the sensors depicted in FIG. 5 during a testing session.
Figure 7:
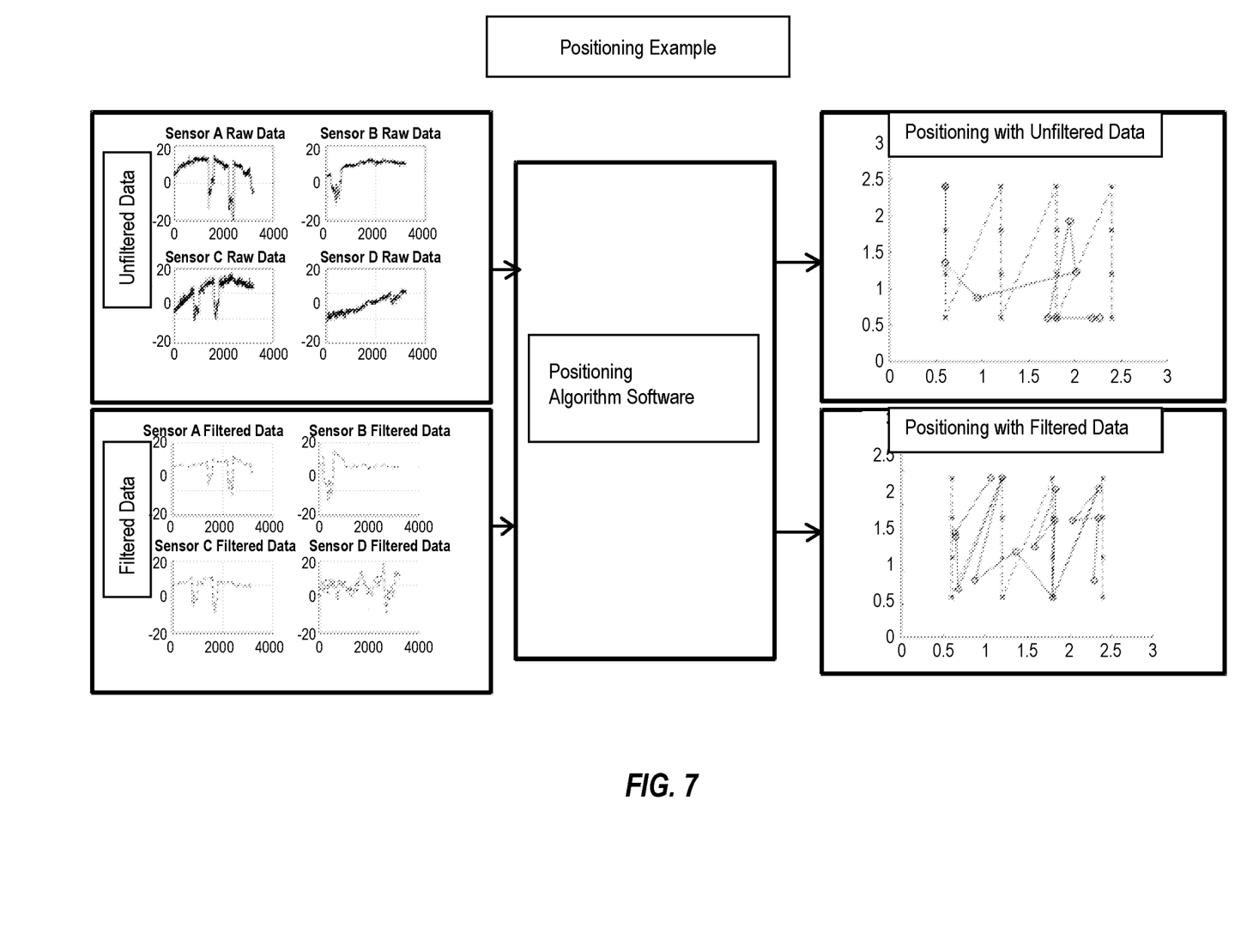
FIG. 7 shows graphs plotting the localization accuracy obtainable during a testing session using the raw and the filtered sensor data, respectively.

In the embodiment shown in FIG. 5-7, the base station receives four streams of digital values from the four sensor nodes in the room, for example one set of new readings every second, through its RF wireless receiver. The wireless receiver of the base station forwards the digital values to the microcontroller of the base station, which in turn sends them through a local serial communication port to a central device (e.g., a personal computer or a dedicated hub device) for further processing. In other words, a system for monitoring a space according to the invention comprises the following parts:
a plurality of capacitive sensors 2 for sensing changes in the status of a space, adapted to electrically interact in a contactless way with a ground surface so that each of said capacitive sensors 2 is adapted to provide a capacitance varying on the basis of said changes, to detect at least a time evolution of said capacitance, and to produce at least a capacitance-depending signal on the basis of said at least a time evolution of said capacitance;
a filtering unit 25 configured for reducing the noise level in said capacitance-depending signals by filtering them, so that corresponding filtered signals are produced;
a central device in signal communication with said capacitive sensors 2, configured for performing (for example cyclically or in reaction to the detection of a significant capacitance change) the following step:
acquiring the filtered signals of each capacitive sensor 2;
determining a position of said object of interest inside said space by inferring at least a distance of said object on the basis of the filtered signals acquired from the sensors that detected said object, and by combining said at least a distance with positional data (also referred as 'positional information') defining the positions of said plurality of capacitive sensors 2 in the monitored space.

The invention also relates to a central device in signal communication with capacitive sensors adapted for sensing changes in the status of a space by electrically interacting in a contactless way with a ground surface so as to provide a capacitance varying on the basis of the changes, and adapted to detect at least a time evolution of the capacitance and to produce a capacitance-depending signal. In an embodiment of the invention, the central device comprises a filtering unit configured for reducing the noise level in said time evolution of the capacitance by filtering the capacitance-depending signal provided by the capacitive sensors, so that corresponding filtered signals are produced. The central device is configured for performing the following steps:
acquiring the filtered signals of each capacitive sensor (2);
determining a position of said object of interest inside said space by inferring at least a distance of said object on the basis of the filtered signals acquired from the sensor that detected said object, and by combining said at least a distance with positional data defining the positions of said plurality of capacitive sensors 2 in the monitored space.

In such embodiment the filtering unit is, at least partially embodied in the central device and can be realized either by a combination of hardware and software elements (for example in a PC or any other electronic processing device) or by a software digital filter. In such a case, the filtering unit is associated with a plurality of capacitive sensors and with the central device; the filtering unit is configured for reducing the noise level present in the capacitance-depending signal provided by a plurality of said capacitive sensors.

In another embodiment of the invention, the filtering unit is not comprised in the central device but is partially or totally embodied in one or more of the capacitive sensors and connected to the central device by a communication link, preferably wireless. In such a case, the invention relates to a central device in signal communication with a filtering unit, the filtering unit being configured for reducing the noise level in the time evolution of the capacitance produced by capacitive sensors by filtering the capacitance-depending signal provided by the capacitive sensors (2), so that corresponding filtered signals are produced; the capacitive sensors (2) are adapted for sensing changes in the status of a space by electrically interacting in a contactless way with a ground surface so as to provide a capacitance varying on the basis of such changes, and adapted to detect at least a time evolution of such capacitance and to produce a capacitance-depending signal. The central device is configured for performing the following steps:

acquiring the filtered signals of each capacitive sensor 2;
determining a position of said object of interest inside said space by inferring at least a distance of said object on the basis of the filtered signals acquired from the sensor that detected said object, and by combining said at least a distance with positional data defining the positions of said plurality of capacitive sensors 2 in the monitored space.

In an embodiment of the invention, an important function of the processing on the central device is to remove the noise from sensor data by applying several sets of digital filters, in case the data received from the capacitive sensors carry too much noise, i.e., are affected by the environmental noise and the capacitive sensors do not (sufficiently) filter out such a noise before outputting them towards the central device. Filtering raw data is an important step that allows our invention to significantly extend the sensing range of small-size sensors, otherwise limited by the signal to noise ratio. The noise can come from different sources (e.g., electrical appliances, static charge on people or objects, temperature or humidity changes) and can afflict sensor measurements in different ways.

In the samples shown in FIG. 6, the solid line is affected by long-term drifts and by high-pitch noise. For example, the noise generated by electric appliances (like the start or stop of a conditioning air system or a refrigerator motor) is often distributed over high frequencies, which are better reduced using a low-pass filter, while the noise introduced by temperature and humidity drifts is generally distributed over very low frequencies, which can be attenuated using a high-pass filter. Depending on the target of interest (e.g., human activities or monitoring of the electric noise in the environment), the corresponding frequencies can be selected for further processing. The Applicant notices that a higher sampling frequency will result in better tracking of fast movement, while increasing power consumption and reducing battery life. The frequency used in this exemplary embodiment of the invention is suitable to track the location in an apartment where a person spends a significant amount of time. Sampling at a higher frequency (e.g., 10 Hz) would more precisely track the movement of the person, but would also have a 10 times shorter battery life. Therefore the choice of the sampling frequency can be adjusted depending on the time resolution needed for the space monitoring and the energy source capacity of the sensors.

The amplitude of the drift can be clearly seen to be much higher than the variations due to changes in the position of the body of the person, which are represented by shifts down followed by shifts up of the level of the signal. The dashed line (filtered data, right side of FIG. 6) shows how most of the signal can be reconstructed by filtering, so that it becomes suitable to be subsequently used by localization techniques to infer the position of the person.

Figure 8:
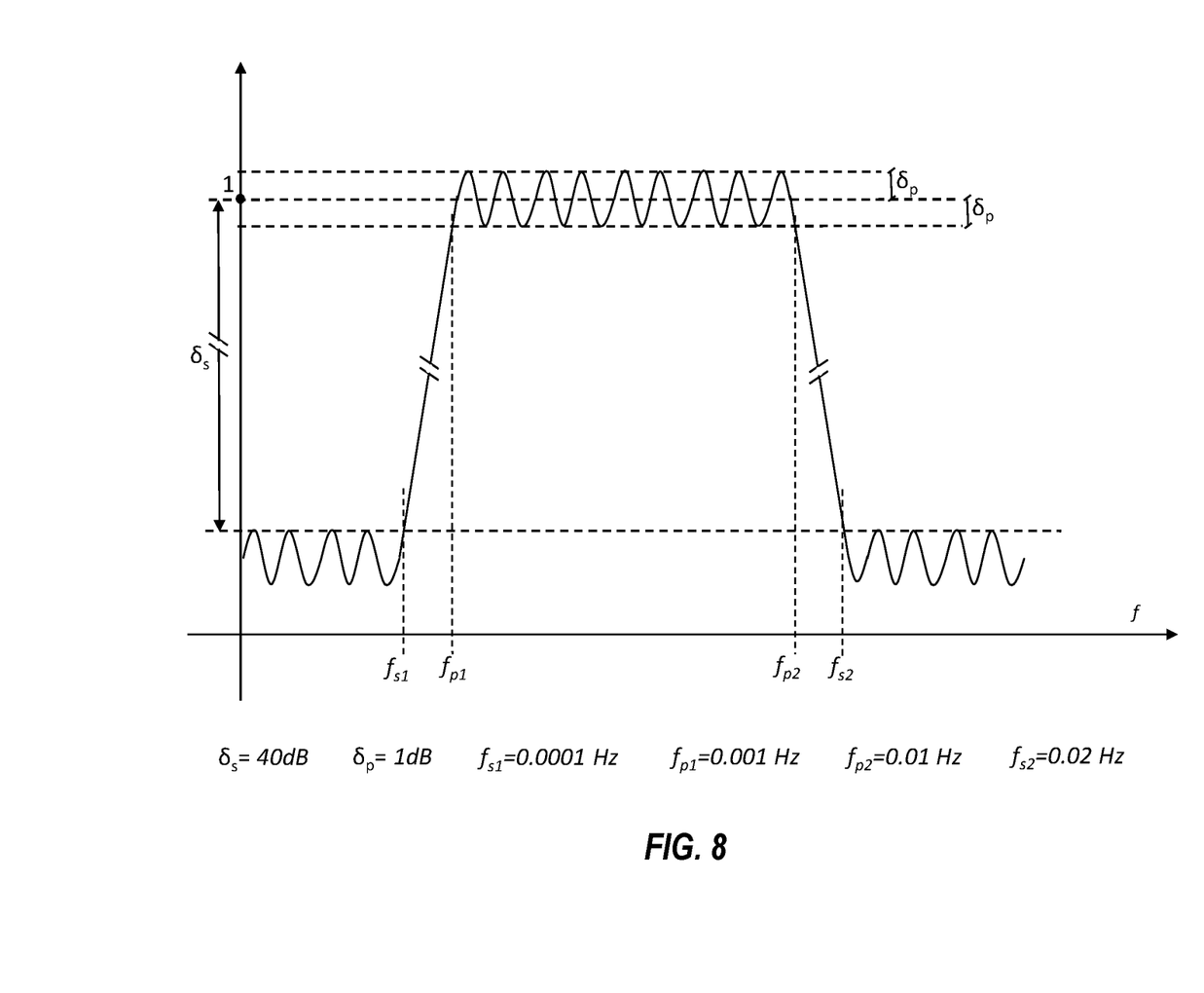
FIG. 8 shows a graph plotting the module of the transfer function of an exemplary pass-band filter used in an embodiment of the invention.

The filters can be implemented separately (cascaded high-pass and low-pass filters) or using band-pass filters. For the localization of a single person in a room, a set of filter parameters may comprise a stop-band frequency (cutoff frequency) of 0.0001 Hz and a pass-band frequency of 0.001 Hz for the high-pass filter, a stop-band frequency (cutoff frequency) of 0.02 Hz and a pass-band frequency of 0.01 Hz for the low-pass filter, and for both filters a stop-band attenuation of 40 dB, maximum allowed ripple in pass-band of 1 dB, and a sampling rate of 1 Hz. In this exemplary embodiment of the invention, both filters are of the Finite Impulsive Response (FIR) equiripple type. The resulting pass-band filter used in this embodiment of the invention is shown schematically in FIG. 8. The Applicant notices that this configuration works well with the sensor nodes in a room having a size of 3 m×3 m. With these parameters, the positioning technique using filter output data can determine the position of the person in the room with a mean error of less than 50 cm.

The filtered sensor data are input to the central device which is configured for running a set of instructions implementing a localization technique. The localization technique estimates the position of the person within the room using the sensor readings (i.e., the filtered signal) as input.

The localization technique operates either in training mode or in localization mode. The purpose of the training mode is to allow the central device to confidently associate a known position of the person in the room with specific values of the filtered sensor data. The purpose of the localization mode is to infer the position of the person in the room from the current filtered sensor data. As the person moves within the room (FIG. 5), the localization technique tracks in real time the position of the person's body.

Note that in all cases the sensors must be placed so that all points of interest fall within the maximum sensing distance of at least one sensor.

By combining the known positions of the sensors with the distance information derived from the filtered signals coming from the excited sensors (i.e., the sensors that detected the object of interest as being in their detection range), the central device is able to determine the position of the object of interest in the monitored space. Such positions can be entered in any way by the installing staff into the device and can be updated in case the sensors are repositioned for any reason.

The training step is essential for this localization mechanism, because it allows one to improve the accuracy and to give a meaningful "label" to "interesting locations" in a room, apartment or building. The kind of training and the kind of "labeling" depends on the final goals and on the characteristics of the room where tracking must take place. For example:

if the goal is to track the exact trajectory of a person within a room, then the sensors can be spread uniformly around the room, for example they can be placed on the walls if the room is small enough so that every point of interest falls within the maximum sensing distance from at least one wall. The same sensor distribution is suitable to detect intrusions by detecting sudden changes in places that normally have a static configuration (e.g., warehouses);

if the goal is to track the daily activity of an elderly person, it is more appropriate to place a sensor near each place where the person is expected to spend a significant amount of time (e.g., a chair, an armchair, a bed), or near a significant location (e.g., a sink, a door). This will ensure greater confidence when identifying these "interesting locations";

if the goal is to detect the presence of persons or objects in dangerous zones for safety applications, the sensors need to be placed such way that all danger zones fall within the range of at least one of the sensors;

if the goal is to detect an abnormal operation or handling of electrical or electronic devices or appliances, then the sensors should be placed so as to detect the distinct electric noise generated during their operation;

if the goal is to detect abnormal movement of electrically conductive objects, then the sensors should be placed to cover at least some part of the trajectory of the objects of interest.

In an embodiment of the invention, the central device is configured to work in an operative mode and in a training mode. During the training mode, the central device is configured to acquire training data generated by associating at least a predetermined position of the object in the monitored space with the filtered signals acquired by the sensors when the object is in said predetermined position. During the operative mode, the central device is configured for determining, on the basis of said training data, the position of said object by selecting the position of the training data associated to the filtered signals that better matches the filtered signals acquired in the training mode. As it will better described later on, such selection is performed for instance by means of a localization technique, such as a K-nearest neighbors or a naïve Bayes.

During the training, several capacitive samples are taken for each sensor when the person is in each position that needs to be "labeled" (e.g., positions p1-p16 in FIG. 5). These samples are associated with the corresponding label, and each localization technique uses this information to later classify a sensor reading as belonging to a "label".

The use of several samples and the application of the filters described above ensure that the labeling process is less susceptible to noise also during the training phase.

With also reference to FIG. 7, it will now be shown the effectiveness of sensor data filtering on the accuracy of the localization of the person in the room. During a training phase, in an exemplary embodiment of the invention, the sensor data was collected while a person was occupying the positions p1, . . . , p16 shown in FIG. 5 in numerical order, as shown in crosses in FIG. 7. The sensors (called node A, B, C, and D) were located on the four sides of the room, also as shown in FIG. 5. In this case, the goal was to track the location anywhere within the room.

On the top row in FIG. 7, the localization technique estimated the position of the person body in the room using the raw, unfiltered sensor data plotted at the top-left in said FIG. 7. The localization result is shown at the top-right in the same Figure, in solid line (movement trajectory) and circles (positions). On the bottom row in FIG. 7, the localization technique estimated the position of the person body in the room using the filtered sensor data plotted at the bottom-left in FIG. 7. The localization result is shown at the bottom-right in the same Figure, in solid line (movement trajectory) and circles (positions).

The positions of the person in the room that are inferred by the localization technique from the filtered data (bottom-right in circles in FIG. 7) are closer to the actual positions of the person in the room (bottom-right in crosses in FIG. 7) than the positions inferred from unfiltered data (top-right in circles in FIG. 7). This shows that adequate filtering of sensor data can significantly extend the sensitivity and accuracy of distance measurement of the sensor, up to distances that allow the use of the capacitive sensor for the considered domain of applications (i.e., indoor person localization), without requiring the adoption of larger sensing plate.

The localization technique that is used in the preferred embodiments is the k-Nearest Neighbor (k-NN), with k=1. The steps of the technique are the following:

receiving an input data set, which preferably comprises four values of frequency (f1, f2, f3, f4), wherein each value is read by means of a distinct sensor 2;

computing at least one distance, preferably the Euclidean distance, between the input data set and each data point in the training set;

selecting, on the basis of said at least one distance, the data point in the training set that is closest to the input data set;

returning the room position corresponding to this closest training point.

As an alternative, a naïve Bayes (NB) localization technique can also be used instead of the 1-NN technique. In this case, the central device calculates the statistical mean and standard deviation of the data points for each room position during the training phase. Next, when the system is in an operating condition, the central device estimates the probability that a given data point in the input data set belongs to each room position, and assigns this data point to the room position with the highest probability.

The empirical results obtained by the Applicant are summarized in the following table:

| Plate Size | k-NN (k = 1) | NB (Naïve Bayes) |
| --- | --- | --- |
| 4 × 4 cm | Unfiltered data error: 1.1 m | Unfiltered data error: 1.1 m |
| | Filtered data error: 0.4 m | Filtered data error: 0.4 m |
| 8 × 8 cm | Unfiltered data error: 1.13 m | Unfiltered data error: 1.15 m |
| | Filtered data error: 0.31 m | Filtered data error: 0.37 m |
| 16 × 16 cm | Unfiltered data error: 0.65 m | Unfiltered data error: 0.81 m |
| | Filtered data error: 0.31 m | Filtered data error:0.24 m |

The above techniques can be used for inferring the presence of a person close to locations of interest in the monitored area, such as an armchair, sink, bed, or door. The localization techniques are trained by providing them with the filtered readings of the sensors while the person occupies different locations of interest. The filtering of raw sensor data can be the same as for the localization of the person in an arbitrary position within the space of the room. These filtered readings sets are memorized in the memory unit of the central device in association with the corresponding location, called training point; the number and locations of the location-readings associations, i.e., the training points, depend on the largeness of the space to be monitored and on the desired spatial resolution. More training points in a given space increase the spatial resolution of the location estimation and lower the mean error of such estimation, in the assumption that all other measuring conditions remain unchanged. The price to be paid can be a more complex training phase with NB, or a more complex localization phase and a higher occupation of the memory unit with k-NN.

Indoor localization of persons can be used for various applications. One application is assisted living, where the localization data inferred using the system of sensors (such as the location, the time spent in each location and the trajectory or temporal succession of locations) can be used by an upper level technique, which is implemented by a second set of instructions that is executed by the central device, to infer and check patterns of behavior in order to flag and alert for any deviations that may be due to a condition of the person that needs assistance. Therefore, in an assisted living application, the sensor 2 or the system according to the invention is used for monitoring the position of at least a person. In order to reduce battery consumption, if the goal is to identify where the person spends most of the time, and what are the patterns of movement from location to location, a low sampling frequency, preferably from 0.1 to 1 Hz, can be used.

Safety applications can use sensor data which are post-processed in a similar way in order to detect the presence of persons in dangerous zones. The zones can be designated as dangerous in different ways: permanently, time-based, or in correlation with external events, such as machinery operation cycles, or the like.

The sensor system can be used also for security applications. For example, it can be used to detect changes in places that are supposed to be static, such as merchandises stored in warehouses. Such changes can be due to human or robotic unauthorized intrusion (which may require security checks), or be due to falling objects (which may require maintenance checks). For such applications, the raw sensor data are filtered the same way as for indoor person monitoring. However, the training of the localization techniques is aimed to recognize only the stable configuration of the monitored space, and any sudden changes should be flagged as anomalous. Therefore, in a safety application, the sensor 2 or the system according to the invention is used for monitoring the position and/or the status of at least an object or a person.

Other security applications can detect unauthorized accesses to a monitored flat or house. For instance, the monitoring system based on sensors can detect that the occupants left the place and the system can enter an anti-intrusion mode in which any sudden change in the sensed capacities depending on the position change of objects or the presence of human bodies should trigger an alert. Alternatively, the occupants could manually switch the system to the anti-intrusion mode. In another operation mode, the system can monitor the capacitive sensors surveying perimetral access points of the monitored space, such as windows and doors, besides the location of the monitored occupant. Any sudden change at any of these access points can be flagged as unauthorized access. For these operation modes, the system requires changes only to the upper processing layers, which are normally used to infer the behavior of the person from location data. Therefore, in a security application, the sensor 2 or the system according to the invention is used for monitoring the presence of unauthorized people in a space. In those anti-intrusion modes, the central device memorizes the filtered readings of the involved transducers at the activation instant and periodically verifies whether the capacitive filtered readings received in real time by the sensors 2 correspond to those previously memorized, taking into account the admitted tolerances.

So, in an embodiment of the invention, the acquisition of the filtered signals derived from the capacitance-depending signals produced by the capacitive sensors 2 as well as the position determination are repeated periodically by the central device with a certain time period; the central device is configured to monitor the time evolution of said filtered signals in order to either trace the electrical state of the object of interest when it is detected to be static and/or to trace the path of said object when it is detected to be in motion. In some embodiments of the invention, this period can be varied for instance in order to monitor more frequently the time evolution of the capacitance if a certain event occurred (i.e., an intrusion) and/or for better tracing the position of a new object detected within the monitored space. This period change can be triggered either automatically by the central device basing on certain instructions memorized in the non volatile memory of the device taking into account the operating conditions of the device; alternatively or additionally, it can be varied by the user of the device if the application of the system requires such a change, for example the time period can be increased for energy-saving purposes.

In some embodiments of the invention, the central device is configured to detect the appearance in monitored space of a new object causing a capacitance variation detected by at least one of the capacitive sensors 2 and to monitor as well the position and/or the electrical state of the new object that becomes the object of interest.

In another embodiment, the central device is further configured to detect whether at least one of said filtered signals is comprised either in a first set or in a second set, wherein said first set contains filtered signals that are considered by the central device as a normal, non-alerted status of said monitored space, whereas said second set contains filtered signals that are considered by the central device as an abnormal, alerted status of said monitored space, and wherein the central device is also configured for signalling about detecting a normal or an abnormal status of said space. A typical application is an anti-intrusion application where during the training phase a certain set of filtered signals are associated by the central device to a non-intrusion status and any other set of such signals not comprised in such first set is considered by the central device as signalling an intrusion. Of course some tolerances are preferably introduced in the values of the filtered signals considered as a normal non alerting status for avoiding false alarming. Additionally the temperature, humidity or other physical parameters influencing the capacitance that are independent from an intrusion can be measured in order to exclude that slow but considerable changes in the capacitance detected by the sensors 2 cause a false alarm.

In some embodiments, the anti-intrusion application of the capacitive monitoring system can have different desired characteristics with respect to the body position monitoring application. For example, it should be able to detect the intrusion of different entities than those usually present in the monitored environment (e.g., pets, shorter or taller persons). Moreover, in order to track a fast moving intruder, the sampling frequencies should be increased and the filter parameters must be changed with respect to the assisted living scenario, thus decreasing the battery life. This may be acceptable if the absences during which the intrusions must be detected are typically shorter than the time spent at home by the person, or a more powerful battery must be used to support this functionality. In such cases it is advantageous that the characteristics of the filters (e.g., cut-off frequency, pass-band or stop-band values) acting on all or only some of the sensors are reprogrammable or reconfigurable, so as to adapt the detecting characteristics of the system to the different requirements due to the new application of the same hardware. Advantageously, such characteristics can be memorized in the memory of the central device associated with the corresponding application so that when an application switch is necessary the suitable configuration can be uploaded on a sensor over the air, for example from the central device in order to reconfigure the system.

The operation of electrical appliances can be correlated with the normal behavior of the person in the apartment where the appliances are located, to enhance the behavioral pattern discovery or detect abnormal operation of the appliances. In order to detect the operation of these appliances, they need to be in range of at least one sensor, and the raw sensor data should be processed using additional sets of filters, which are aimed to detect the specific noise patterns that are produced by these electrical appliances (e.g., the start/stop of the compressor of the fridge, fridge door open, or TV set on).

From the output of these specific filter chains, the upper processing layer can infer the state of the appliances and correlate them with the behavior of the person. Deviations can be notified as either assistance being needed for the person (e.g., erratic access to fridge may indicate irregular eating) or for the appliance (e.g., excessive operation of fridge compressor may be due to its door left open or a malfunction).

Other Embodiments and Generalizations

In the embodiment described so far some peripheral sensing devices 2 carry out the initial steps of the changes detection in the status of the monitored space, while a central device performs the last of such steps. This is a preferred solution based on the current performance of the signal processing techniques that allow certain power consumption for a given processing throughput. Of course, other task distributions are possible among the devices being part of the capacitive sensing system and, consequently, other kinds of devices are involved in the process. The power/energy consumption per processing unit is continuously lowering and therefore new configurations of the sensing system can become convenient in the future.

For example, part of the filtering operations can be performed in the peripheral sensing devices 2 and the data can be sent already partially or totally filtered to the central device, which could just perform the final positioning process of the human body or, more generally, the final status estimation of the monitored space based on the data cumulatively received from the sensing devices 2.

In another embodiment, at least one of the sensors 2 of the capacitive monitoring system for a given space could also act also as central device. In this embodiment, such kind of more complex sensor would embody all the blocks necessary for performing the status estimation of the monitored space, like the positioning of a human body moving inside such space. It would receive and process also the unfiltered capacitance-depending readings of the other sensors monitoring other portions of the same space and consequently the I/O unit would receive such data and filter them together with the readings performed locally.

Conversely and equivalently, a central device can also act as a sensing device and comprise a sensing device and therefore a transducer. In such a case there would be only one CPU performing all the signal processing operations on the capacitance-depending signal locally coming from the capacitive plate.

At least some of the digital signal processing (like oversampling, averaging, decimation, filtering) and of the status estimation can be performed by a dedicated software running on a processor of a general purpose computer or other computing device comprising a processor, such as a tablet, a PC, a smart phone, a note book, or the like. Some of such processing can be performed by a dedicated firmware embodied in any form in a dedicated electronic chip optimized for this purpose. This second embodiment is preferred in case of small assembled electronic devices to be positioned in an environment with very small impact on the existing infrastructures like walls, lamp posts and so on.

It should be noted that the invention does not find applications only in the monitoring of the position and activity of human individuals, but also in general in the monitoring of the environment which can typically be indoor, but also outdoor. For example, the system according to the invention can be used as in a surveillance equipment of a building or an apartment to be monitored in absence of its inhabitants. In such a case, in the installation and training phase, the capacitive sensors would be placed in determined locations of the environment, typically in correspondence of peripheral and normally stationary elements of the building like walls, furniture, door frames. After that, the set of sensor signals is monitored in non-alerting situations, i.e., in absence of any human being in the environment and any other event that is considered as non-alarm triggering (slow temperature, pressure, humidity or lighting variations, activity of refrigerator or washing machine motors). In such application, the operative parameters of the filters are adjusted in order to eliminate the capacitance variations due to events considered unimportant. Instead, some testing can be made in order to ascertain that the capacitance variations caused by human or animal intruders entering the area covered by the capacitive sensors cause the monitoring system to notify the surveillance operators of a possible intrusion event.

If, for example, the user wants to monitor also the correct functioning of an electric appliance (like a refrigerator) installed in a household location, then during a training phase the installing personnel would monitor in isolation the capacitance variations caused by the normal working of the appliance in different environmental conditions. In the example of the refrigerator, the high-frequency capacitance variations caused by the start and stop transitions of its cooling motor is monitored at different ambient temperatures considered normal and the corresponding minimum and maximum capacitance discontinuities are established as normally occurring in a certain time interval (e.g., a day or a certain amount of hours). If no start and stop events are detected within a certain period, the refrigerator is presumably out of order for some reason; if such events occur too often, then presumably some of the refrigerator doors have been left mistakenly open. So, what is considered noise in certain applications and is to be suppressed by the filters, instead becomes a useful signal to be passed by them in other applications.

Another typical application of the invention is the automatic on and off switching and/or control of an electric appliance, like a lighting device, e.g., a lamppost or an indoor light bulb, for both indoor and outdoor environments. One or more capacitive sensors are located in the area illuminable by the device and possibly in close proximity of the entrances or passages of such area. First, when the presence of at least one human being is detected, the monitoring system causes the lighting device to switch on; when all human beings are detected to have left the illuminable area, the lighting device is switched off, preferably after a certain time interval from the last positive detection instant. Alternatively, especially in case of outdoor applications, e.g., lamppost, the lighting device is always switched on and the lighting strength is increased during the detection of human beings in the illuminable area. If the lighting spot is directive, additionally, the main light beam can be directed to the location where the presence of a human being is detected in the area. This smart lighting system can be applied both for public outdoor lighting systems for open spaces (streets, gardens, parking areas, or the like) and for private anti-intrusive illumination systems.

The present description has tackled some of the possible variants, but it will be apparent to the man skilled in the art that other embodiments may also be implemented, wherein some elements may be replaced with other technically equivalent elements. The present invention is not therefore limited to the explanatory examples described herein, but may be subject to many modifications, improvements or replacements of equivalent parts and elements, without departing from the basic inventive idea, as set out in the following claims.

The invention claimed is:

1. A system for localizing at least one object of interest in a monitored space, said monitored space being a tridimensional free-to-air space, comprising:
a plurality of capacitive sensors for sensing changes in a status of said monitored space, each capacitive sensor comprising one sensing plate operating in load mode that causes a capacitance changing with a distance from said at least one object of interest, said at least one object of interest being used as a second plate, and that produces a plurality of capacitance-depending signals on a basis of said distances, wherein said sensing plates are small-sized with respect to sizes of said monitored space,
a filtering unit configured for reducing a noise level in said capacitance-depending signals by filtering them for increasing a sensing range of the capacitive sensors, so that filtered signals are produced, and
a central device in signal communication with said capacitive sensors, configured for:
acquiring the filtered signals of each capacitive sensor, and
determining a position of said at least one object of interest inside said monitored space by inferring a plurality of said distances of said sensing plates from said at least one object of interest on a basis of the filtered signals acquired from the sensing plates that detected said at least one object of interest, and by combining said plurality of distances with positional data defining positions of said plurality of sensing plates in the monitored space.

2. The system according to claim 1, wherein said central device is configured to work in an operative mode and in a training mode, and wherein during said training mode the central device is configured to acquire training data generated by associating at least a predetermined position of said at least one object of interest in said monitored space with the filtered signals acquired by said capacitive sensors when said at least one object of interest is in said predetermined position.

3. The system according to claim 2, wherein, during said operative mode, the central device is configured for determining, on a basis of said training data, the position of said at least one object of interest by selecting a position of the training data associated to the filtered signals that better matches the filtered signals acquired in the training mode.

4. The system according to claim 3, wherein the selection of the position is performed by means of a localization technique.

5. The system according to claim 1, wherein said filtering unit comprises a plurality of filters each associated with one of said capacitive sensors and with said central device, said filters being configured for reducing the noise level present in one of the capacitance-depending signals provided by said capacitive sensors.

6. The system according to claim 1, wherein said filtering unit is associated with said plurality of capacitive sensors and with said central device, said filtering unit being configured for reducing the noise levels present in the capacitance-depending signals provided by said plurality of said capacitive sensors.

7. The system according to claim 1, wherein the transfer function of the filtering unit can be varied by means of a switching command, and wherein said central device is configured for generating said switching command.

8. The system according to claim 1, wherein the central device is configured for acquiring said filtered signals and determining the position of said at least one object of interest cyclically with a time period, and said central device is configured to monitor said filtered signals in order to either trace an electrical state of the at least one object of interest when it is detected to be static and/or to trace a path of said at least one object of interest when it is detected to be in motion.

9. The system according to claim 8, wherein said time period can be varied.

10. The system according to claim 1, wherein the central device is further configured to detect an appearance in the monitored space of a new object causing a capacitance variation detected by at least one of said capacitive sensors and to monitor a position and/or an electrical state of said new object that becomes the object of interest.

11. The system according to claim 1, wherein the central device is further configured to detect whether at least one of said filtered signals is comprised either in a first set or in a second set, wherein said first set contains filtered signals that are considered by the central device as a normal, non-alerted status of said monitored space, and said second set contains filtered signals that are considered by the central device as an abnormal, alerted status of said monitored space, and wherein the central device is also configured for signalling about detecting a normal or an abnormal status of said monitored space.

12. The system according to claim 4, wherein the localization technique comprises a K-nearest neighbors or a naïve Bayes.

13. A central device for being part of a system for localizing at least one object of interest in a monitored space, said monitored space being a tridimensional free-to-air space,
said central device comprising a communication interface configured to receive capacitive-depending signals produced by a plurality of sensing plates operating in load mode that cause a capacitance changing with a distance from said at least one object of interest, said at least one object of interest being used as a second plate, and that produces a plurality of capacitance-depending signals, wherein said sensing plates are small-sized with respect to sizes of said monitored space,
said central device comprising:
a filtering unit configured for
reducing a noise level in said capacitance-depending signals by filtering them for increasing a sensing range of the capacitive sensors, so that corresponding filtered signals are produced,
acquiring the filtered signals of each capacitive sensor, and
determining a position of said at least one object of interest inside said monitored space by inferring a plurality of distances of said sensing plates from said at least one object of interest on a basis of the filtered signals acquired from the sensing plates that detected said at least one object of interest, and by combining said a plurality of distances with positional data defining positions of said plurality of capacitive sensing plates in the monitored space.

14. A central device for being part of a system for localizing at least one object of interest in a monitored space, said monitored space being a tridimensional free-to-air space, said central device comprising a signal communication interface with a filtering unit configured for reducing noise levels in a plurality of capacitance-depending signals by filtering said capacitance-depending signals provided by capacitive sensing plates, so that corresponding filtered signals are produced for increasing a sensing range of the capacitive sensing plates, wherein said sensing plates are small-sized with respect to sizes of said monitored space, and wherein said capacitive sensing plates operating in load mode cause a capacitance changing with a distance from said at least one object of interest, said at least one object of interest being used as a second plate, and produces said plurality of capacitance-depending signals, said central device being configured for:
- acquiring the filtered signals of each sensing plate from said filtering unit, and
- determining a position of said at least one object of interest inside said monitored space by inferring a plurality of distances of said sensing plates from said at least one object of interest on a basis of the filtered signals acquired from the sensing plates that detected said at least one object of interest, and by combining said plurality of distances with positional data defining positions of said sensing plates in the monitored space.

15. A method for localizing at least an object of interest in a monitored space, said monitored space being a tridimensional free-to-air space, comprising:

- a detection phase, wherein a plurality of capacitance-depending signals is detected by means of a detecting unit in communication with a plurality of sensing plates, wherein said sensing plates operating in load mode cause a capacitance changing with a distance from said at least one object of interest, said at least one object of interest being used as a second plate, and produces said plurality of capacitance-depending signals on a basis of said distances, wherein said sensing plates are small-sized with respect to sizes of said monitored space,
- a filtering phase, wherein filtered signals are produced by filtering said capacitance-depending signals by means of a filtering unit, so that a noise level in each of said capacitance-depending signals is reduced, by increasing a sensing range of the capacitive sensing plates,
- an acquisition phase, wherein said filtered signals are acquired by a central device, and
- a position determination phase, wherein a position of said at least one object of interest inside said monitored space is determined, by means of said central device, by inferring a plurality of distances of said sensing plates from said at least one object of interest on a basis of the filtered signals acquired from said sensing plates detecting said at least one object of interest, and by combining said plurality of distances with positional data defining positions of said plurality of sensing plates in the monitored space.

16. A computer program product which can be loaded into a memory of a digital processing device, and which comprises portions of software code for executing the method according to claim 15.

* * * * *